United States Patent
Mie et al.

(10) Patent No.: US 11,147,894 B2
(45) Date of Patent: Oct. 19, 2021

(54) DEVICE FOR TRANSPORTING A HOLLOW BODY, INSTALLATION PROVIDED WITH SUCH DEVICES, AND METHOD FOR CONVEYING A HOLLOW BODY ATTACHED TO SUCH A DEVICE

(71) Applicant: SIDEL PARTICIPATIONS, Octeville sur Mer (FR)

(72) Inventors: Patrick Mie, Octeville-sur-Mer (FR); Frédéric Lethuillier, Octeville-sur-Mer (FR)

(73) Assignee: SIDEL PARTICIPATIONS, Octeville sur Mer (FR)

( * ) Notice: Subject to any disclaimer, the term of this patent is extended or adjusted under 35 U.S.C. 154(b) by 0 days.

(21) Appl. No.: 14/057,874

(22) Filed: Oct. 18, 2013

(65) Prior Publication Data

US 2014/0044597 A1    Feb. 13, 2014

Related U.S. Application Data

(62) Division of application No. 12/743,486, filed as application No. PCT/FR2008/052074 on Nov. 18, 2008, now abandoned.

(30) Foreign Application Priority Data

Nov. 19, 2007    (FR) ..................... 07 08110

(51) Int. Cl.
*A61L 2/16*    (2006.01)
*B29C 49/42*    (2006.01)
*B29C 49/06*    (2006.01)
*B29C 49/78*    (2006.01)
*B29K 67/00*    (2006.01)
(Continued)

(52) U.S. Cl.
CPC ............ *A61L 2/16* (2013.01); *B29C 49/4205* (2013.01); *B29C 49/78* (2013.01); *B29C 49/06* (2013.01); *B29C 49/12* (2013.01); *B29C 2049/4635* (2013.01); *B29K 2067/00* (2013.01)

(58) Field of Classification Search
CPC . A61L 2/16; B29C 2049/5886; B29C 49/421; B29C 49/4273; B29C 49/4205; B29C 49/4252; B29C 2049/4635
USPC .............. 264/211.12, 211.13, 232, 340, 520; 422/28, 302, 304
See application file for complete search history.

(56) References Cited

U.S. PATENT DOCUMENTS 1,018,046 A * 2/1912 Goldman .................. B08B 9/42
                                                134/199
1,608,634 A * 11/1926 Taylor ....................... A61L 2/07
                                                422/303
(Continued)

FOREIGN PATENT DOCUMENTS

CA    2 312 804 A1    6/1999
DE    43 26 346 A1    2/1995
(Continued)

*Primary Examiner* — Marc C Howell
*Assistant Examiner* — John J DeRusso
(74) *Attorney, Agent, or Firm* — Sughrue Mion, PLLC

(57) ABSTRACT

The invention concerns a device, an installation and a method for conveying a hollow body secured to a transport device, comprising a step of injection of a disinfecting fluid through at least one bore designed to pass through said transport device and opening into the inner volume of the hollow body secured to said transport device.

18 Claims, 2 Drawing Sheets

(51) Int. Cl.
*B29C 49/46* (2006.01)
*B29C 49/12* (2006.01)

(56) References Cited

U.S. PATENT DOCUMENTS

| | | | |
|---|---|---|---|
| 1,880,257 A * | 10/1932 | Rheinstrom | B08B 9/30 134/23 |
| 4,065,286 A * | 12/1977 | Becker | C03B 7/16 65/229 |
| 4,437,985 A | 3/1984 | Hinds et al. | |
| 4,818,212 A * | 4/1989 | Gibbemeyer | 425/529 |
| 4,846,656 A | 7/1989 | Sidel | |
| 4,890,726 A * | 1/1990 | Wissmann | 198/803.12 |
| 5,031,673 A * | 7/1991 | Clusserath | 141/6 |
| 5,792,491 A | 8/1998 | Chaure | |
| 5,803,291 A | 9/1998 | Valles | |
| 5,860,461 A * | 1/1999 | Helmut | 141/326 |
| 6,328,928 B1 | 12/2001 | Schroeder et al. | |
| 6,562,281 B1 * | 5/2003 | Marchau | B29C 49/42 264/532 |
| 6,761,556 B1 | 7/2004 | Pellegatta et al. | |
| 6,984,360 B1 | 6/2006 | Feuilloley et al. | |
| 7,284,778 B1 | 10/2007 | Pellegatta | |
| 7,497,237 B2 | 3/2009 | Till | |
| 7,621,738 B2 | 11/2009 | Doudement | |
| 7,806,680 B2 | 10/2010 | Adriansens et al. | |
| 7,814,940 B2 | 10/2010 | Till et al. | |
| 2003/0000969 A1 * | 1/2003 | Mie | B08B 9/32 222/196 |
| 2004/0208781 A1 | 10/2004 | Hayashi et al. | |
| 2006/0005896 A1 * | 1/2006 | Till | 141/147 |
| 2008/0044510 A1 | 2/2008 | Doudement | |
| 2008/0166440 A1 | 7/2008 | Dujardin et al. | |
| 2008/0296801 A1 | 12/2008 | Zoppas et al. | |
| 2009/0071104 A1 | 3/2009 | Fischer | |
| 2009/0081326 A1 | 3/2009 | Adriansens et al. | |
| 2009/0130268 A1 | 5/2009 | Euler et al. | |
| 2009/0196790 A1 | 8/2009 | Sangi | |
| 2009/0293429 A1 | 12/2009 | Till | |

FOREIGN PATENT DOCUMENTS

| | | |
|---|---|---|
| DE | 199 34 320 A1 | 1/2001 |
| DE | 199 49 692 A1 | 4/2001 |
| DE | 1 99 56 186 A1 | 5/2001 |
| DE | 10 2004 030 956 A1 | 1/2006 |
| DE | 10 2004 030 957 A1 | 1/2006 |
| EP | 0304385 | 7/1988 |
| EP | 0 951 437 B1 | 4/2001 |
| EP | 1 056 481 B1 | 10/2001 |
| EP | 1 037 675 B1 | 11/2002 |
| EP | 0 996 530 B1 | 1/2003 |
| EP | 1 220 787 B1 | 9/2003 |
| EP | 1 144 016 B1 | 12/2003 |
| EP | 1 003 674 B1 | 5/2004 |
| EP | 1 212 187 B1 | 11/2004 |
| EP | 1 614 433 A1 | 1/2006 |
| EP | 1 820 731 B1 | 10/2009 |
| EP | 1 896 329 B1 | 3/2010 |
| EP | 1 729 825 B1 | 6/2011 |
| EP | 1 958 879 B1 | 7/2012 |
| EP | 1 858 560 B1 | 12/2013 |
| FR | 2 706 876 A1 | 12/1994 |
| FR | 2 766 121 A1 | 1/1999 |
| FR | 2 774 912 A1 | 8/1999 |
| FR | 2 789 932 A1 | 8/2000 |
| FR | 2 794 109 A1 | 12/2000 |
| FR | 2 872 805 A1 | 1/2006 |
| FR | 2 882 963 A1 | 9/2006 |
| FR | 2 887 525 A1 | 12/2006 |
| FR | 2 890 061 A1 | 3/2007 |
| JP | 63-307928 | 12/1988 |
| JP | 03-290226 A | 12/1991 |
| JP | 11-048323 | 2/1999 |
| JP | 11-105114 | 4/1999 |
| WO | 99/43607 A1 | 9/1999 |
| WO | 2004/045784 A1 | 6/2004 |
| WO | 2005/037522 A1 | 4/2005 |
| WO | 2006/005694 A1 | 1/2006 |
| WO | 2006/053745 A1 | 5/2006 |
| WO | 2006/095099 A1 | 9/2006 |
| WO | 2007/134803 A2 | 11/2007 |
| WO | 2007/140883 A1 | 12/2007 |
| WO | 2008/017410 A1 | 2/2008 |

* cited by examiner

DEVICE FOR TRANSPORTING A HOLLOW BODY, INSTALLATION PROVIDED WITH SUCH DEVICES, AND METHOD FOR CONVEYING A HOLLOW BODY ATTACHED TO SUCH A DEVICE

CROSS REFERENCE TO RELATED APPLICATIONS

This is a divisional application of U.S. patent application Ser. No. 12/743,486, filed May 18, 2010, which is the National Stage of International Application No. PCT/FR2008/052074 filed Nov. 18, 2008, claiming priority based on French Patent Application No. 0708110, filed Nov. 19, 2007, the disclosures of which are hereby incorporated by reference.

FIELD OF THE INVENTION

The invention relates in general to the field of manufacturing receptacles made of thermoplastic material obtained after heating and blow molding of a hollow body commonly called a preform, and it relates more particularly to a conveying system comprising a series of transport devices that are each furnished with at least one gripping member designed to carry a preform for the purpose of making it travel in a vertical position inside the installation.

Therefore, the invention applies to the in-line processing installations for the manufacture or processing of preforms made of thermoplastic material such as PET, in which installations said preforms are moved individually one after the other with the aid of transport devices capable of holding them by their neck, so as to leave their body free for the purpose of heating.

DESCRIPTION OF THE PRIOR ART

Routinely, a preform takes the general shape of a tubular cylindrical body closed at one of its axial ends and extended at its other open end by a neck already having the final shape of the neck of the final receptacle and a collar extending substantially radially. In the rest of the description, "receptacle provided with a neck" is understood to be any hollow body having a neck, namely preforms, from which receptacles are manufactured by blow molding or stretch-blow molding, that is to say receptacles having their final shape and having to undergo an additional process (such as a step of labeling or filling).

In the particular case of the transport of preforms, in order to take them to temperature by heating prior to the blow molding step, it is necessary to provide a transfer device making it possible to take each preform by its neck ("gripping") in order to move it into a heating zone, usually a heat-conditioning tunnel oven, in which zone the body of said preform is to be heated to the glass-transition temperature of the thermoplastic material, while remaining at a temperature below the crystallization temperature.

To achieve this transfer, it is known practice to use transport devices furnished with gripping members which comprise a mandrel suitable for being engaged inside the neck of the preform (internal gripping) and which holds the latter simply by adhesion because of the presence of the forces of pressure and of friction.

In document FR 2 706 876, in the name of the Applicant, a device for the internal gripping of preforms from a gripping head having a split-ring end is proposed.

According to the same principle of internal gripping, it is known practice, as proposed in document FR 2 794 109 in the name of the Applicant, to produce a system for conveying preforms formed of a set of transport elements each comprising a gripping device furnished at its end with an annular split ring formed of several sectors; when the ring is engaged internally in the neck of a preform, the sectors that are forced radially outward by elastic means are capable of pressing on the inner cylindrical surface of the neck.

Alternatively, it is also possible for the preform to be gripped on the outer face of its neck (external gripping) as described, for example, in document FR 2 882 963 in the name of the Applicant.

In installations for the treatment in straight lines for manufacturing containers or for the treatment of hollow bodies, it is sometimes necessary to apply inside the hollow bodies treatment actions with fluid and/or appropriate interactions with fluids, for example sterilization actions or fumigation by injecting an disinfecting fluid.

These interactions occur upstream or downstream from the conveyor device, because its conveying members close the hollow bodies.

When this preform enters the heat-conditioning oven, the preform undergoes a rotation on itself in order to allow an even heating over the whole outer surface of the preform. When a preform is loaded into the mold, both internally and externally, it is possible for the latter not to be axially aligned with the gripping head.

In this case, because the preform is out of line and because of its rotary movement on itself, the body of the preform, and in particular its end, is capable of coming into contact with the heating lamps of the oven and of causing considerable damage by breaking them and also, sometimes, the preform can catch fire.

Therefore, in order to prevent these incidents, such as the damaging of the oven heating lamps, it is necessary to provide, before they enter the oven, an operation of releasing of the preforms, that is to say an operation which consists in ejecting all the preforms that are capable of causing incidents when they pass into the heating oven.

This releasing operation makes it possible, in a general manner, to prevent heating preforms which would have a design defect on entering the oven.

Document FR 2 872 805 in the name of the Applicant describes a system for releasing preforms.

Optical detection means are provided in order to determine which preforms are to be released and, under the effect of an appropriate command apparatus, such as a programmable controller, an ejection member intervenes in order to take away the preforms in question, which then fall into a recovery bin for example.

This system, although giving full satisfaction, is nevertheless complex to apply and, above all, it hampers the production rates of the installation; specifically, the response time of the ejection member, for the purpose of the releasing, is relatively long.

Moreover, because of the current production rates and therefore the speed of progress of the preforms, it is not possible to eject a single preform because, due to the response time of the pneumatic command means, several preforms are affected by the ejection member and, in general, routinely three successive preforms are on average ejected.

Because of the cost of manufacturing the preforms, and in order to prevent the scrapping of preforms correctly placed on the gripping head or having no defect, it would be of particular value to produce a device for releasing preforms that allows the releasing of only the preform that is incorrectly secured or is incorrectly formed; said device being able to be applied at high rates of travel of the preforms. It would also be of particular value to produce a releasing system that could also be applied to the releasing of the preforms but and also to any type of hollow body.

Moreover, because of this releasing of several preforms placed one beside the other, there are considerable free spaces in the preform-conveying chain (three successive gripping heads). These large spaces between the preforms, in the oven, disrupt the heating of the other preforms when they pass in front of the lamps of said oven; the result of this is defects in the evenness of heating of the preforms.

Moreover, a current change in the context of the manufacture of preforms tends to reduce the dimensions of the collar, which becomes increasingly thin and increasingly wide, and hence more frequent gripping problems.

Therefore, it would also be particularly advantageous to produce a releasing system that is not dependent on the size of a collar provided on the neck of the hollow body.

SUMMARY OF THE INVENTION

The present invention therefore proposes to solve the various problems associated with the prior art with the aid of a system for releasing hollow bodies that makes it possible to release a single preform at high conveying rates, which system also does not depend on the dimensional characteristics of the collar of said preform.

According to a first of its aspects, the present invention relates to an installation for conveying preforms to a processing unit such as a heating oven in which they are taken to an appropriate temperature in order subsequently to be formed by stretch-blow molding, which installation comprises:

gripping members which are carried by an endless conveyor chain and which are each furnished with a gripping head in order to carry said preforms and in order to transfer them into said heating oven, at least one detection system placed on the path of said preforms upstream of said heating oven, which detection system, such as a shape-recognition camera, selects the preforms that are likely to cause incidents in said heating oven, such as, for example, preforms the alignment of which does not correspond with that of the main axis of their gripping head, means for detaching each selected preform from its gripping head, an apparatus, such as a programmable controller, to command the ejection of the selected preform according to the information originating from said detection system, means for retrieving the ejected preforms, and it comprises means for applying a pressure to the inside of the selected preform, on its bottom, and in particular a sufficient pressure to overcome the forces of adhesion between said selected preform and its gripping head, in order to detach them.

Still according to the invention, the means capable of applying a pressure in the selected preform, on its bottom, consist:

of a nozzle capable of spraying a jet of pressurized fluid at the bottom of said selected preform, and, of an orifice in the shape of a bore arranged in the member and in the gripping head of said selected preform, said jet of pressurized fluid being administered when said bore passes in front of said nozzle.

According to another stipulation of the invention, the bore, into which the pressurized fluid intended for the selected preform is injected, comprises an upstream aperture in the form of a funnel which has a narrowing of its cross section in the direction of the downstream aperture.

Still according to the invention, the programmable controller used for commanding the injection of the pressurized fluid comprises a program arranged in order to establish an appropriate phase for the administration of said pressurized fluid to the selected preform, which phase extends for a period substantially greater than the time taken by said selected preform to pass in front of the spraying nozzle so as to ensure an injection time of said pressurized fluid into the bore that is long enough to ensure the ejection of said selected preform.

The invention also relates to the method for releasing preforms while they are conveyed to the heating oven, in order to eliminate each preform capable of creating an incident during its passage in said heating oven, said method consisting:

in monitoring the preforms which pass by, before they enter said heating oven, in order to detect, in said preforms, a flaw capable of causing incidents in said heating oven, in detaching each preform recognized as undesirable from its gripping head, upstream of said heating oven, by applying an appropriate force to the inside of the undesirable preform, on its bottom, and in particular a sufficient force to overcome the forces of pressure and of friction that are applied between said undesirable preform and its gripping head, in collecting the rejected preform in an appropriate container.

Still according to the invention, the releasing method consists in separating the undesirable preform from its gripping head via an injection, in an appropriate bore of said gripping head, of a jet of pressurized fluid which penetrates the inner volume of said undesirable preform.

According to another stipulation of the invention, the releasing method consists in anticipating the passage of the undesirable preform in order to trigger the injection of the pressurized fluid into said preform and it also consists in maintaining this injection of said pressurized fluid at least until the gripping head has passed in front of the nozzle for spraying said fluid.

BRIEF DESCRIPTION OF THE DRAWING

The present invention will now be described with the aid of an example that is only illustrative and in no way limiting of the scope of the present invention.

DETAILED DESCRIPTION OF THE INVENTION

Figure 1:
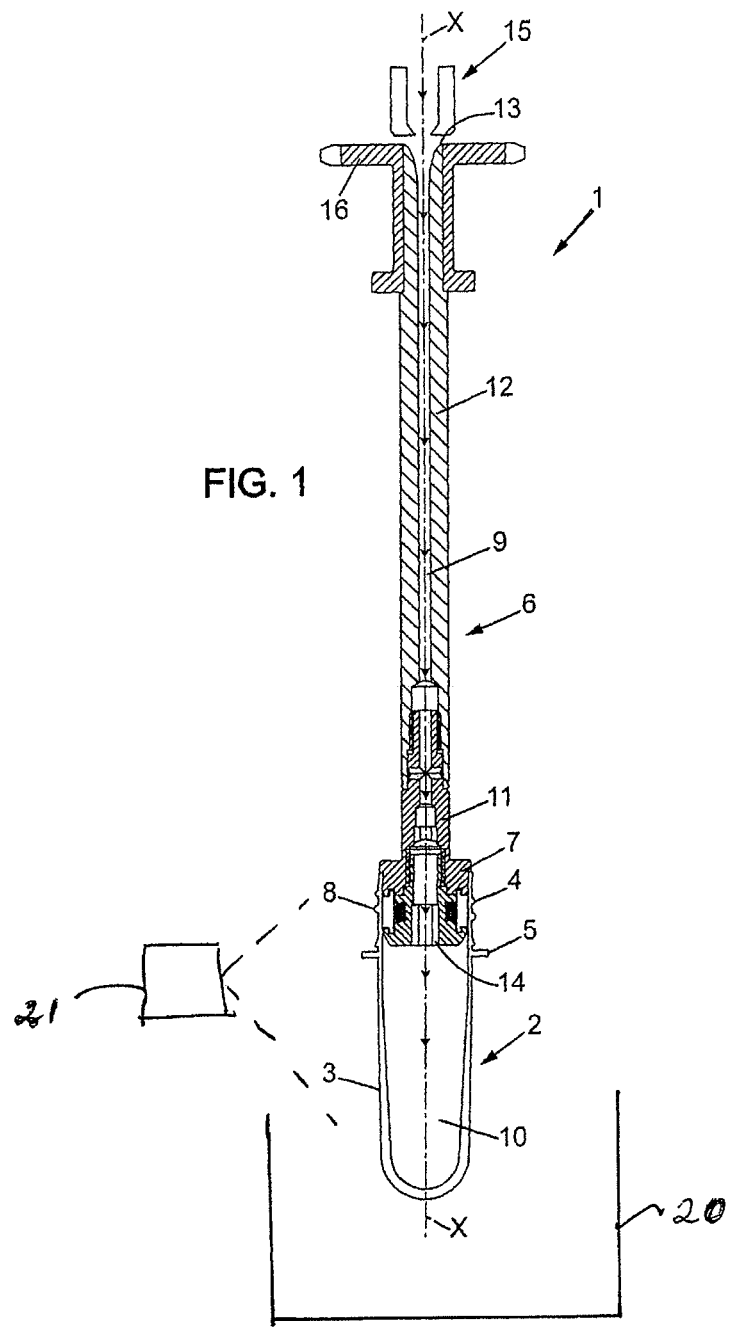
FIG. 1 represents a view in axial section of a device for transporting and gripping a hollow body according to the invention, which device, in cooperation with a blowing nozzle, makes it possible to carry out an operation of releasing of the preforms.

In a simplified manner, FIG. 1 represents a view in axial section of a device 1 for transporting a hollow body, such as a preform 2 made of thermoplastic material. The preform 2 has a body 3 extending in a substantially longitudinal manner and a neck 4 separated from the body 3 by a collar 5 extending in a substantially transverse direction.

The transport device 1 comprises a gripping member 6 with a gripping head 7 capable of being secured to the preform 2, and preferably, of being secured in a sealed manner to its neck 4.

Shown in FIG. 1 is an "internal" gripping of the preform 2 and of the type described in the aforementioned document FR 2 794 109, that is to say that the gripping head 7 is inserted inside the neck 4 and therefore presses on the inner face of the neck 4.

However, it should be noted that the principle according to the invention applies equally to an "external" gripping of the preform 2, that is to say when the gripping head 7 presses on the outer face of the neck 4, in general pressing on the thread 8 of the neck 4.

According to the invention, the gripping member 6 has at least one bore 9 opening through the gripping head 7.

Therefore, according to a first application of the invention, the preform 2 is capable of being separated from the gripping head 7 by injection of a pressurized fluid (preferably compressed air at a pressure of the order of at least several bar, from 2 to 5 bar) in the bore 9 then opening into the closed volume 10 which is formed by the body 3 of the preform 2 secured to said head 7 and to do so whether the volume 10 is perfectly sealed or not.

Alternatively, the inside of the preform 2 can be disinfected by injection of a disinfecting fluid into the bore 9 opening into the closed volume 10 which is formed by the hollow body 3 secured to said head 7.

In general, it is possible to inject any type of fluid through the bore 9 having an appropriate interaction and/or a desired processing action on the closed volume 10 which is formed by the hollow body 3 secured to the head 7.

The bore 9 is therefore designed passing through the gripping member 6, in a substantially rectilinear manner inside said member 6. This bore 9 is of generally cylindrical shape and is formed centrally in the member 6, that is to say that considering the gripping member 6 defines a main gripping axis X-X, the axis X-X relative to which it is determined whether the preform 2 is correctly secured to the gripping head 7 and in line with the latter, then the bore 9 is substantially formed coaxially with the main gripping axis X-X.

More precisely, the gripping member 6 comprises a mandrel 11 having said gripping head 7 and a gripping rod 12 to which said mandrel 11 is attached, preferably in a removable manner.

The bore 9 is therefore formed and hollowed both in the gripping rod 12 and in the mandrel 11.

In order to limit the pressure losses during the injection of the pressurized fluid in the bore, said bore is designed to be substantially rectilinear inside the gripping member and it is advantageously of a general shape that is substantially cylindrical.

More precisely, the bore 9 has an upstream aperture 13 for the injection of a fluid and a downstream aperture 14 in the gripping head 7. The upstream aperture 13 has a narrowing of its cross section in the direction of the downstream aperture 14.

At the upstream aperture 13, in order to allow a maximum quantity of fluid to be channeled, directed and to enter the bore 9, it is therefore provided that the upstream aperture 13 has a larger cross section than the cross section of the majority of the bore 9, and in particular larger than the cross section of the downstream aperture 14.

Even though what is shown in FIG. 1 is a transport device 1 with a single central bore 9, it is also possible to provide several bores 9, for example placed concentrically with the main gripping axis X-X, or to provide a bore 9 that is divided into several secondary bores all opening into the gripping head 7.

Figure 2:
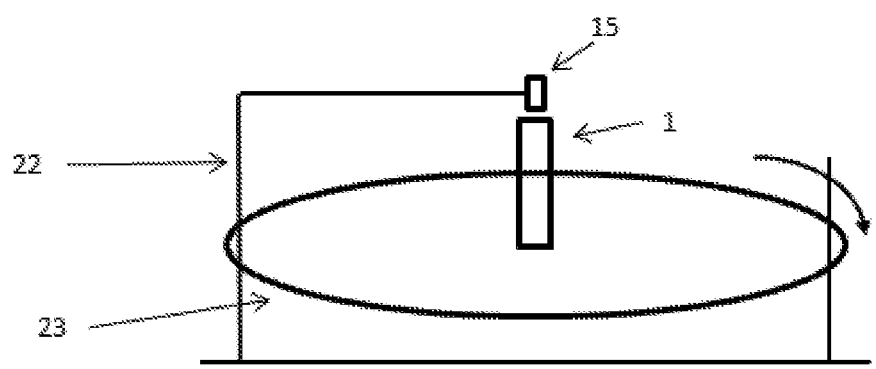
FIG. 2 represents a schematic view of the blowing nozzle on a chassis of an installation, and an endless conveyor that carries the transport devices.

The present invention also relates, according to a second of its aspects, and in a more general manner as shown in FIG. 2, to an installation for conveying hollow bodies 2 comprising a plurality of transport devices 1 which travel in line one after the other on an endless chain 23, of a type that is known per se, as can be seen, for example, in the aforementioned document FR 2 872 805.

The conveying installation comprises means for injecting a jet of fluid such as a pressurized blowing fluid, for example at a pressure of between 2 and 5 bar, in the knowledge that, on this type of machine, a pressure is available of up to 40 bar, which means for injecting blowing fluid are directed toward a point of passage of at least one bore 9 formed internally in a transport device 1 when it travels on the endless chain 23.

Preferably, the injection means take the form of a blowing nozzle 15 which is fixed, attached to a chassis 22 of the installation, not shown, which nozzle 15 is therefore directed toward a point of passage of the upstream aperture 13 of the bore 9 during the travel of the transport devices 1 associated with the endless chain 23.

In order to prevent too great a loss of the fluid injected through the nozzle 15, said nozzle 15 is situated facing a point of passage of the upstream aperture 13 of the bore of the transport devices 1 and it is only a very short distance from this upstream aperture 13, for example of the order of a millimeter, or even a few millimeters.

According to one application of the invention, the conveying installation may also comprise detection means 21 such as a shape-recognition camera or other monitoring means, in order to reveal a defect of alignment of the body 3 of the preform 2 with the main gripping axis X-X and the axis of the gripping head 7, whereby it is determined whether the preform 2 transported by said gripping head 7 must be separated from the latter by the injection of the pressurized blowing fluid.

The command of this injection may be carried out via a programmable controller which receives and processes the information originating from the detection means mentioned above.

This programmable controller comprises a program arranged to organize the command of the injection of the pressurized fluid into the preform that is recognized as having a defect that is likely to cause incidents in the oven for heating these preforms.

The arrangement of the injection program comprises a phase that is appropriate for the administration of the pressurized fluid to the selected preform, which phase extends, for example, for a period that is substantially greater than the time taken by said selected preform to pass in front of the spraying nozzle so as to ensure an injection time of said pressurized fluid into the bore that is sufficiently long to ensure that said selected preform is ejected.

This injection phase is also arranged to allow an anticipation of the triggering of the injection of the pressurized fluid into said undesirable preform facing the passage of said undesirable preform in front of the nozzle 15 for spraying said fluid and for maintaining this injection of said pressurized fluid at least until the gripping head 7 has completely passed in front of said nozzle 15 for spraying said fluid.

The invention therefore makes it possible, in general, to produce a method for conveying a preform 2 secured to a transport device 1, said method comprising a step of injection of a fluid through at least one bore 9 designed to pass through said transport device 1 and opening into the inner volume 10 of the body 3 of the preform 2 secured to said transport device 1.

According to another form of application of the invention, a disinfecting fluid is injected through the bore 9. Alternatively, a pressurized fluid is injected, which makes it possible to separate the hollow body 2 from the gripping head 7.

Therefore, in summary, according to one application of the invention, it is detected, with the aid of the detection means, whether a preform 2 is out of alignment with the axis X-X or has a manufacturing defect. It is then determined, with the aid of the programmable controller and of appropriate programs and/or computing means, when the transport device 1 with this preform, and more precisely its bore 9, will pass in front of the means 15 for injecting blowing fluid, in order then to command the injection of this fluid in order to release the preform (or any hollow body secured to a gripping head 7), which may then be collected in a container 20.

The response time of the fluid injection means is markedly faster than the response times of the piston-based pneumatic means according to the aforementioned prior art, which makes it possible to release only one preform at a time.

Therefore, according to a first application of the invention, the hollow body is capable of being separated from the gripping head by injection of a pressurized blowing fluid in the bore then opening into the closed volume that is formed by the hollow body secured to said head.

Alternatively, the inside of the hollow body can be disinfected by injection of a disinfecting fluid into the bore opening into the closed volume that is formed by the hollow body secured to said head.

More generally, the invention can find its place on an installation for transporting necked receptacles, where it is sometimes necessary to release the hollow bodies that have a defect, such as, for example, on leaving the preform blow molding unit.

The invention claimed is:

1. A method of conveying a preform for heating the preform prior to blow molding a container from said preform, comprising:
   providing an installation that includes a chassis and an endless conveyor including a transport device, the transport device being provided with a bore having an upstream aperture, wherein the endless conveyor conveys the upstream aperture along a path;
   providing an injecting nozzle attached to the chassis of the installation such that the injecting nozzle is fixed in position and directed to a predetermined point of the path; and
   conveying the preform that is secured to the transport device, prior to a blow molding stage, the bore having a downstream aperture that opens into an inner volume of the preform secured to said transport device;
   while the injecting nozzle is fixed in position, injecting a disinfecting fluid into the upstream aperture of the bore of said transport device during the travel of the upstream aperture, by projecting the disinfecting fluid out of the injecting nozzle toward the predetermined point of the path when said upstream aperture is passing the predetermined point of the path;
   channeling the projected disinfecting fluid through the bore and into the inner volume of the preform; and
   moving the preform into which the disinfecting fluid has been channeled to a heating zone, the heating zone heating a body of said preform comprising thermoplastic material to a glass-transition temperature of the thermoplastic material.

2. The method according to claim 1, wherein, during the injecting, a gap is maintained between the injecting nozzle and the upstream aperture.

3. The method according to claim 1, wherein the endless conveyor is an endless conveyor chain.

4. The method according to claim 1, wherein the endless conveyor is an endless conveyor belt.

5. The method according to claim 1, wherein the transport device comprises a gripping member that grips an interior of the preform during the step of channeling the disinfecting fluid into the preform.

6. The method according to claim 5, wherein the gripping member grips the interior of the preform in the heating zone.

7. A method of sterilizing a hollow body, comprising:
   conveying the hollow body, along a traveling path of an installation for conveying the hollow body, using a transport device on an endless belt or endless chain of the installation; and
   injecting a disinfecting fluid through a bore of the transport device while the hollow body is being conveyed by the transport device, wherein the bore opens into an inner volume of the hollow body secured to the transport device so as to inject the disinfecting fluid in the hollow body, and
   moving the hollow body into which the disinfecting fluid has been injected to a heating zone, the heating zone heating said hollow body that comprises thermoplastic material to a glass-transition temperature of the thermoplastic material; and
   wherein the injecting uses an injecting nozzle, the injecting nozzle being fixed so that the injecting nozzle faces a predetermined point of the traveling path of the bore during injecting of the disinfecting fluid so as to direct the disinfecting fluid toward the predetermined point of the traveling path of the bore as the bore travels past the predetermined point.

8. The method according to claim 7, wherein the transport device includes a gripping member that grips an interior of the preform, wherein the bore is disposed in the gripping member, and the gripping member grips the preform during the injecting and, after the injecting, the gripping member grips the preform during a heating of the preform.

9. A method of conveying a preform, comprising:
   providing an installation that comprises a chassis and an endless conveyor having a transport device that travels along a conveying path, wherein the transport device is an elongated member having a gripping head at a first end with an outlet aperture, an inlet aperture at a second end opposite the first end, and a fluid conduit extending from the inlet aperture to the outlet aperture, and wherein the outlet aperture is smaller than an opening of the preform at a neck of the preform;
   providing an injecting nozzle fixed in position relative to the chassis and directed to a predetermined position on the conveying path;
   removably coupling the gripping head to the neck of the preform, so that the outlet aperture opens directly into an internal volume of the preform;
   prior to blow molding the preform, conveying the preform with the transport device along the conveying path and, as the transport device passes the predetermined position, injecting a disinfecting fluid into the inlet aperture by ejecting the disinfecting fluid from the injecting nozzle toward the predetermined position when the inlet aperture passes the predetermined position, so that the disinfecting fluid is channeled through the fluid conduit and the outlet aperture and into the internal volume of the preform.

10. The method according to claim 9, wherein the fluid conduit has a length that is greater than a length of the preform from a bottom of the preform to a top of the neck of the preform.

11. The method according to claim 9, wherein the gripping head is removably coupled to an internal surface of the neck of the preform.

12. The method according to claim 9, wherein the gripping head, when coupled to the preform, obstructs the opening of the preform neck.

13. The method according to claim 9, comprising, after injecting the disinfecting fluid, conveying the preform with the transport device to a heating zone and heating the preform to a glass transition temperature of a thermoplastic material of the preform while the preform remains coupled to the transport device.

14. The method according to claim 9, comprising a plurality of the transport devices that travel in line one after the other along the conveying path.

15. The method according to claim 9, wherein, when injecting the disinfecting fluid into the inlet aperture, a gap is maintained between the injecting nozzle and the inlet aperture.

16. The method according to claim 9, wherein, when injecting the disinfecting fluid into the inlet aperture, a gap is maintained between the injecting nozzle and the transport device.

17. The method according to claim 9, wherein the endless conveyor is an endless conveyor chain.

18. The method according to claim 9, wherein the endless conveyor is an endless conveyor belt.

* * * * *